United States Patent [19]

Kitajima

[11] Patent Number: 5,443,988

[45] Date of Patent: Aug. 22, 1995

[54] METHOD FOR HIGH SPEED ANALYSIS OF A DRY ANALYTICAL ELEMENT

[75] Inventor: Masao Kitajima, Saitama, Japan

[73] Assignee: Fuji Photo Film Co., Ltd., Kanagawa, Japan

[21] Appl. No.: 138,503

[22] Filed: Aug. 30, 1993

[30] Foreign Application Priority Data

Sep. 2, 1992 [JP] Japan .................................. 4-234775

[51] Int. Cl.$^6$ ............................................. G01N 35/02
[52] U.S. Cl. ........................................ 436/46; 422/58; 422/66; 436/44; 436/49
[58] Field of Search ................................ 436/43–44, 436/46–47, 49, 164; 422/58, 66, 68.1

[56] References Cited

U.S. PATENT DOCUMENTS 4,954,319  9/1990  Koizumi et al. .................. 436/44

*Primary Examiner*—Lyle A. Alexander
*Attorney, Agent, or Firm*—McAulay Fisher Nissen Goldberg & Kiel

[57] ABSTRACT

A high speed analyzer for a dry analytical element comprising a movable sample tray onto which the dry analytical element is placed, a sample-pipetting apparatus which spots a plurality of samples onto the dry analytical element placed onto the movable sample tray, an incubator which dries the dry analytical element onto which the samples have been spotted, a reagent-pipetting apparatus which spots a plurality of measuring reagent solutions onto the dry analytical element which has already been dried and a measuring part which measures a plurality of the dry analytical elements wherein reaction proceeds or has already been finished, and evaporation-preventing members which are attached to the dry analytical element onto which the reagents have been spotted to prevent evaporation of moisture from the spotted parts, and a method for measuring a plurality of analytical items of samples using the same. By utilizing the above analyzer, a large number of samples can be analyzed in various analytical items simultaneously rapidly.

8 Claims, 2 Drawing Sheets

METHOD FOR HIGH SPEED ANALYSIS OF A DRY ANALYTICAL ELEMENT

BACKGROUND OF THE INVENTION

This invention relates a high speed analyzer capable of measuring a plurality of analytical items of a large number of samples using a dry analytical element not containing a part or the whole of reagents necessary for the analysis of the object component, and a method for measuring the samples using the same.

Dry analysis is the analytical method using a dry analytical element which is formed of filter paper or a multilayered material composed of one or a plurality of water-permeable layers laminated onto a support into which all reagents necessary for analyzing object component are incorporated. In the dry analysis, operation is simple, and nevertheless, a high analytical accuracy can be obtained. Accordingly, the analysis has recently been developed energetically.

Various measuring instruments (analyzer) for measuring the degree of reaction proceeding on the dry analytical element mounted in a frame to form an anlytical slide have been developed, and the measuring instruments are, in general, composed of a slide supply for supplying each slide to a sample-spotting part successively, an incubator for progressing the detecting reaction in the analytical element wherein the sample has been spotted, and a measuring part for measuring the analytical element wherein the incubation is continued or has been finished. The spotting of each sample to the analytical slide is carried out by manual operation.

SUMMARY OF THE INVENTION

An object of the invention is to provide a means for decreasing a cost for measuring a large number of samples.

Another object of the invention is to provide a means for analyzing a large number of samples at high speed.

Another object of the invention is to provide a means for analyzing various analytical items of a sample simultaneously.

The present invention provides a high speed analyzer for a dry analytical element which has achieved the above objects, comprising a movable sample tray onto which the dry analytical element is placed, a sample-pipetting apparatus which spots a plurality of samples onto the dry analytical element placed onto the movable sample tray, an incubator which dries the dry analytical element onto which the samples have been spotted, a reagent-pipetting apparatus which spots a plurality of measuring reagent solutions onto the dry analytical element which has already been dried and a measuring part which measures a plurality of the dry analytical elements wherein reaction proceeds or has already been finished, and evaporation-preventing members which are attached to the dry analytical element onto which the reagents have been spotted to prevent evaporation of moisture from the spotted parts.

The present invention also provides a method for measuring a plurality of analytical items of samples which has achieved the above object, which comprises using the above high speed analyzer, wherein said dry analytical element comprises a plurality of reaction zones comprising a porous spreading layer, a hydrophilic polymer layer and a water-impermeable support laminated in this order and not containing the measuring reagents, and each reaction zone being formed so that spotted solutions do not permeate into adjacent reaction zones and the reaction proceeds independently at each reaction zone.

DETAILED DESCRIPTION OF THE INVENTION

Figure 1:
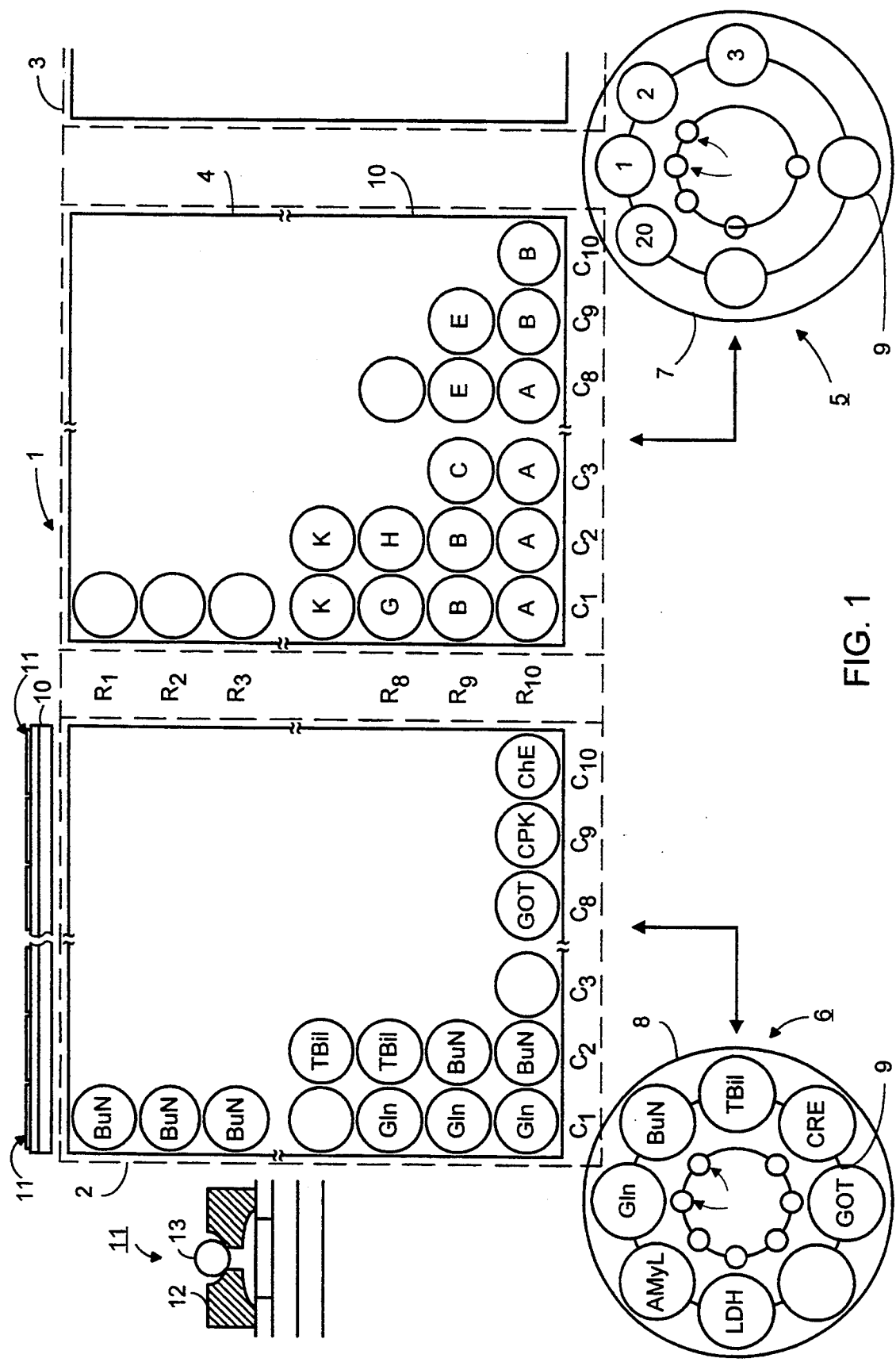
FIG. 1 is a schematic view illustrating the construction of a high speed analyzer which embodies the invention.

The movable sample tray comprises a support plate for placing the dry analytical element at a prescribed position, and the support plate is arranged so as to travel the pipetting position for spotting a sample, the incubator, the pipetting position for spotting the measuring reagent solution and the measuring part for measuring an optical change occurred in the analytical element in this order. It is preferable to arrange so that the playtime between respective stations for spotting a sample, incubating, spotting the measuring reagent solution or measuring the optical change is made as short as possible. For that purpose, it is preferable to incorporate the incubator into the pipetting part of the sample, to arrange so that the optical change can be measured at the pipetting part of the measuring reagent solution, and the like. The number of the movable sample trays is preferably plural, particularly the same as the number of stations.

The dry element may be used in a form of a large sheet as it is. Or alternatively, roll film which bears heat cut reaction zones may be used. The sheets or roll films may not be fixed to a supporting plate, but in this case they should be transfered at a prefixed interval by some other means, e.g. performation or friction rolls, for placing the dry analytical element on the surface of the support plate. In the case that the dry analytical element is used in the form of a large sheet as it is, when the dry analytical element is a multilayer analytical element, the spreading area can be controled by providing a spreading layer or water absorption layer having a constant area at each sample spotting part. A preferable method is to divide a large sheet of the dry analytical element into a plurality of reaction zones by grooves formed by heat cutting so that spotted solutions do not permeate into adjacent reaction zones, described later.

The sample-pipetting apparatus spots each sample with constant portions at regular intervals. The sample-pipetting apparatus may be provided with a plurality of pipetting devices so that one row of sample spots can be pipetted at once, or may be provided with one pipetting device which successively travels to repeat pipetting. As the means for drawing a constant liquid amount, microtips, microsyringes and the like are utilizable. One or a plurality of samples are spotted onto one movable sample tray. There is a case that samples are different at each spotting. A suitable spotting amount of sample is 1 to 100 $\mu l$, preferably 2 to 10 $\mu l$.

The incubator is an apparatus for drying all samples spotted onto the dry analytical element after spotting of all samples has been finished. Thereby, it is possible to carry out the reaction occurring by spotting the measuring reagent under a constant liquid amount to develop color under fixed conditions. Electric heating type incubators are convenient. Suitable drying conditions with heating are, for example, at 30° to 60° for 1 to 5 minutes.

The reagent-pipetting apparatus may be similar to the sample-pipetting apparatus. The measuring reagent is composed of one or a plurality of reagents. There is a case that the measuring reagent solutions are different at each spotting.

After the measuring reagent solution is spotted, the evaporation-preventing member is attached to each spotted part of the dry analytical element immediately. The evaporation-preventing member prevents evaporation of moisture therefrom, and it may be a cap, a film sealing, an electromagnetic piece or the like.

The cap covers at least the entire porous spreading layer at each reaction zone, preferably up to the hydrophilic polymer layer or the support, of the dry analytical element. Suitable material for forming the cap is siff moisture-impermeable materials, and include various thermoplastic resins, such as polyethylene, polypropylene, polycarbonate and polystyrene, thermosetting resins, inorganic materials such as metals and ceramics. Among them, thermoplastic resins are preferable because of excellent processibility. A suitable thickness depends on the size of the reaction zone and the like, and in general, it is in the range of 50 to 200 μm. The cap may be of reusable type, but a throwaway type is preferable.

The film sealing covers almost the entire upper surface of each reaction zone. Suitable materials are similar to those for the above cap, and a suitable thickness is in the range of 100 to 500 μm. A peelable adhesive is coated onto the reverse side of the film sealing. The adhesive side of the film sealing is superimposed on the upper surface of the reaction zone, i.e. the upper surface of the porous spreading layer, and is adhered with pressing lightly.

The electromagnetic piece is formed of a material capable of detaching by maneuvering magnetic force, in general, a ferromagnetic material. The evaporation-preventing member may be formed of one member in a form of cap which covers at least the porous spreading layer or in a form of plate which covers almost the entire upper surface of the porous spreading layer. The member may be composed of two members consisting of a frame made of a material which is not adsorbed by magnetic force and an electromagnetic piece which closes the opening of the frame.

The measuring part measures the change of optical density of each analytical element once or plural times successively or after a predetermined period after spotting the measuring reagent solution. A reflection optical densitometer is commonly used for the measurement.

The dry analytical element applied to the invention lacks a part or the whole of the measuring reagent necessary for the object analytical reaction. When the analyte itself is in a detectable state, such as hemoglobin or bilirubin, chemical reaction is not promised. The measuring at the measuring part may be conducted by any method, such as fluorometry, emmission photometry, magnetic analysis or the like, as well as measuring optical density. Besides, the detection can be made more accurate and sure by adding another reagent after the reaction has been fixed. As the dry analytical element, there are test papers, multilayer analytical elements and so on.

As the test paper, there are various types for whole blood, for plasma/serum, for urine, for diluted samples, and the like.

The multilayer analytical element has at least one liquid-permeable porous layer, and may have further one or more liquid-permeable layers which may be either porous or nonporous.

It is preferable to use two or more multilayer analytical elements (reaction zones) in order to improve analytical accuracy. By spotting a standard solution to another multilayer analytical element parallel to spotting a sample, analytical accuracy can further be improved.

A preferable multilayer analytical element comprises a water-impermeable support, a hydrophilic polymer layer and at least one porous spreading layer laminated in this order.

The porous spreading layer has a function to spread components contained in an aqueous liquid sample in plane without uneven distribution and to supply them to the hydrophilic polymer layer at a constant rate per an unit area, and may be composed of every nonfibrous or fibrous porous material known for the spreading layer of conventional dry analytical elements. Examples of the spreading layer include nonfibrous isotropic microporous medium layers represented by membrane filter (blushed polymer) disclosed in U.S. Pat. No. 3,992,158, nonfibrous porous layers represented by continuous space-containing three dimentional lattice grain structure layer where polymer particulates are joined at spots by a water-nonswelling adhesive disclosed in U.S. Pat. No. 4,258,001, porous layers composed of woven fabric disclosed in U.S. Pat. No. 4,292,272, GB 2,087,074A, etc., porous layers composed of knitted fabric disclosed in EP 0,162,302A, various filter papers, glass fiber filter papers, nonwoven fabrics and the like.

In the case that the dry analytical element is divided into a plurality of reaction zones by grooves formed by heat cutting, the porous spreading layer is formed of a thermoplastic material, such as porous membranes formed of cellulose derivative (DAC, TAC, NC, HMC (hydroxymethyl cellulose), HEC (hydroxyethyl cellulose), etc.), porous membranes formed of ethylene or ethylene derivative polymer or copolymer, e.g. polyethylene, polypropylene, polystyrene, plyvinyl chloride, etc., porous membranes formed of polyethylene terephthalate, polycarbonate, polysulfone, etc., porous membranes formed of vinyl polymers or copolymers of acrylic acid, methacrylic acid or esters thereof, and the like. On the other hand, as nonthermoplastic porous membranes, there are porous membranes formed of a condensation polymer, such as nylon, polyamide or polyurethane, porous membranes formed of inorganic material particulates, such as glass particulates or diatomaceous earth, joined by a small amount of polymer, porous membranes formed of polytetrafluoroethylene, filter paper, glass fiber filter paper and the like, and they are unsuitable in the case of dividing the dry analytical element by grooves formed by heat cutting.

The spreading layer may be composed of two or more microporous layers as disclosed in EP 0,166,365A, EP 0,226,465A, etc. As to the multilayer anlaytical element wherein two or more spreading layers are superposed, it is necessary to have the construction that all layers are integrally laminated at the time of sample spotting, but it is not necessary to be integrated in the subsequent processes. Optionally, the anlaytical element can be used in the state that the first spreading layer is separated from the second spreading layer.

The spreading layer may contain a nonionic, anionic, cationic or ampholytic surfactant in order to accelerate spreading of a sample. Besides, it may contain a spreading controller, such as hydrophilic polymer for the purpose of controlling spreading. Furthermore, it may contain all or a part of various reagents for accelerating the object detecting reaction or reducing or inhibiting interfering reactions.

A suitable thickness of the spreading layer varies according to material, structure and the like, and is in the range of 10 to 500 μm, preferably 50 to 300 μm, more preferably 80 to 200 μm.

According to analytical items, etc., the analytical element may be composed of the above porous spreading layer laminated onto a water-impermeable support alone. However, by providing a hydrophilic polymer layer between the porous spreading layer and the support, accuracy and reliability can be improved greatly.

When the thickness of the hydrophilic polymer layer is thin, not more than 50 μm, preferably not more than 20 μm, the layer is not necessary to be thermoplastic. For example, gelatin, polyvinyl alcohol and their partially crosslinked ones are preferable hydrophilic polymers for the invention.

The hydrophilic polymer layer may be composed of various known polymers which are water-soluble, swellable and hydrophilic and are used for conventional dry analytical elements. The hydrophilic polymer is generally a natural or synthetic hydrophilic polymer having a swelling ratio in the range of about 1.5 to about 20 times preferably from about 2.5 to about 15 times at water absorption at 30° C. Examples of the hydrophilic polymer are gelatines, such as acid-treated gelatin and deionized gelatin, gelatin derivatives, such as phthalated gelatin and hydroxyacrylate-graft gelatin, agarose, pullulan, pullulan derivatives, polyacrylamide, polyvinyl alcohol and polyvinylpyrrolidone. Instead of the hydrophilic polymer layer, porous polymer membrane having hydrophilic surface can be used.

A suitable thickness of the hydrophilic polymer layer is about 1 to 100 μm, preferably about 3 to 50 μm, more preferably about 5 to 30 μm. It is preferred that the hydrophilic layer is substantially transparent. The hydrophilic polymer layer may contain all or a part of various reagents for accelerating the object detecting reaction or reducing or inhibiting interfering reactions.

The water-impermeable support may be a known water-impermeable support used in conventional dry analytical elements, and includes a transparent film made of polyethylene terephthalate, polycarbonate of bisphenol A, polystyrene, cellulose ester, such as, cellulose diacetate, cellulose triacetate or cellulose acetate propionate, or the like. The thickness of the support is usually in the range of about 50 μm to about 1 mm, preferably from about 80 μm to about 300 μm. The support is usually light-transmissive, but in the case of measuring from the spreading layer side, it may be colored or may be opaque. The support may be provided with an undercoating layer on its surface in order to strengthen the adhesion of the hydrophilic polymer layer.

In the case that the liquid sample to be spotted is whole blood, the dry analytical element is preferably provided with a layer which remove substantially all or at least a part of blood cells by filtration. For that purpose, porous spreading layer having this function may be selected, and porous spreading layers formed of fibrous materials, such as woven fabrics disclosed in U.S. Pat. No. 4,292,272 and knitted fabrics disclosed in EP 0 162 302A are useful.

The dry analytical element may be provided with a light-shielding layer or a filtering layer as disclosed in U.S. Pat. No. 4,042,335.

The dry analytical element may be provided with a layer which removes substantially all blood cells by filtration separate from the porous spreading layer. Preferable layers therefor include porous layers disclosed in U.S. Pat. No. 4,486,537, EP 0 166 365A, and Japanese Patent Application Nos. 60-256408, 60-279859, 60-279860, 60-279861.

The dry analytical element may be provided with a light-reflecting layer, for example, between the spreading layer and a registration layer. The light-reflecting layer shields the color of sample solution spotted onto the spreading layer, particularly red color of hemoglobin in the case of whole blood sample and yellow color of bilirubin, when detectable change (color change, coloration, etc.) produced in the registration layer, water absorption layer or the like is measured by reflection photometry from the side of the light-transmissive support side, and also functions as a background layer. The light-reflecting layer is preferably a water-permeable layer wherein light-reflecting particulates, such as titanium dioxide or barium sulfate, are dispersed using a hydrophilic polymer as the binder. Preferable binders are gelatin, gelatin derivatives, polyacrylamide and the like. A curing agent may added to curable polymer such as gelatin.

In the dry analytical element, light-reflecting particulates such as titanium dioxide are optionally added to the spreading layer, registration layer or the like.

A water absorption layer may be provided between the support and the registration layer. A blood cell-filtering layer or other filtering layer may be provided between the registration layer and the spreading layer. In addition, the blood cell-filtering layer or other filtering layer may be provided between the light-reflecting layer and the registration layer of the spreading layer.

The plurality of reaction zones may be completely separated from each other, or the support may be not separated and the other layers are separated. The plurality of reaction zones can be arranged by putting individual analytical element pieces which may be provided with the support with a suitable space, or by heat cutting the hydrophilic polymer layer and the porous spreading layer provided on the common support by a blade to form grooves which divide into respective reaction zones. In the latter case, it is preferable that the porous spreading layer is formed of a thermoplastic material, and the above layers are heat cut by using a blade which has been heated to a temperature not lower than the softening point of the thermoplastic material of the porous spreading layer.

The heat cutting may be curried out by using a blade made of a metal such as brass which is heated by electricity, by using a blade made of a metal such as titanium, iron or aluminum which is mounted to an ultrasonic osillator and heated by vibrational energy up to a temperature not lower than the softening point of the thermoplastic material, by irradiating laser beam to heat in a prescribed pattern, or the like.

In every case, a suitable blade thickness is 0.4 to 2 mm, preferably 0.6 to 1.7 mm, more preferably 0.8 to 1.3 mm. When the blade is too thin, the distance between out faces formed by the heat cutting is insufficient. When the blade is too thick, lumps remain on the support, and accordingly unpreferable.

A suitable area of each reaction zone is about 10 to 1,000 mm$^2$, preferably 20 to 200 mm$^2$, particularly preferably 25 to 80 mm$^2$.

The blade forming the grooves by fusion may be either a rotary blade or a straight blade.

A further preferable method is of using a double-edged blade having a V shape section and fusing with moving one or both of the dry analytical element and the blade.

In the case of irradiating laser beam, irradiation conditions are sufficient to be set so that liquid leakage does not occur at the fused groove portion and the support is not cut entirely. For example, in the case of carbon dioxide gas laser, such a heat cut groove can be formed under the conditions at an output of 10 to 25 W and a heat cutting speed of 8 to 10 m/min.

Although the blade angle is not limited, a preferable blade angle is to form a groove of which the width of the upper end, i.e. the space between the upper edges of the porous spreading layer formed by cutting, becomes about 0.1 to 2 mm, preferably about 0.4 to 1.2 mm. A preferable blade angle is 60±15 degrees. If the space is too narrow, when the measuring reagent solution is supplied, the solution occassionally overflows beyond the groove. A preferable blade length is, for example, 0.5 to 7 cm in view of the convenience for preparation and handling of the blade.

Upon heat cutting, the porous spreading layer is preferably rendered flat or convex. In the case of flat form, the dry analytical element or the blade is moved in the longitudinal direction of the blade. In the case of convex form, for example, the support of the dry analytical element is fixed to the periphery of a drum, and then, the drum is rotated while the blade is contacted the porous spreading. By the relative movement between the blade and the dry analytical element, a heat cut groove portion moves to the rear of the blade, the heat cut face is sufficiently fused, the generation of striginess is prevented, and protrusion of the porous spreading layer at the heat cut end is prevented to improve flatness.

The heat cutting temperature is set preferably so that not only the porous spreading layer but also the surface of the support partially melt. In the case of using polyester as the material of the porous spreading layer and the support, a suitable condition is at 400° to 500° C. at a moving speed of about 10 m/min. In general, a suitable fusing temperature is about 100° to 800° C., preferably about 200° to 600° C., more preferably about 300° to 500° C.

The grooves formed by heat cutting are preferably formed up to the surface of the support. In principle, when the porous spreading layer is cut by fusion and the hydrophilic polymer layer is also cut, mixing of measuring reagent solutions does not occur. However, taking the flatness of the dry analytical element into consideration, it is difficult to make such a condition constant. Accordingly, it is preferable to form the grooves formed by heat cutting up to the surface of the support in the depth of 5 to 60 μm, preferably 10 to 45 μm. When the depth is too deep, although the separation is complete, flatness is degraded. Moreover, careful handling is required, because the dry analytical element is liable to be separated into pieces.

It is also possible to form a plurality of grooves formed by heat cut simultaneously by using a plurality of blades. For example, the dry analytical element in a form of web is conveyed by using a drum, and the plurality of blades are set at the rotating part of the drum to form the plurality of grooves in the longitudinal direction of the web. Subsequently, the dry analytical element is put on a table, and one or a plurality of blades are moved in the cross direction of the web to form the grooves formed by fusion in a gridiron pattern.

One or more layers of the dry analytical element can contain one or more arbitrary components, such as surfactant, solvent for coloring agent, buffer, binding agent, hardening agent and the like. The incorporating amount of the above components may be similar to the amount usually added to the conventional dry analytical element. Representative components are disclosed in U.S. Pat. No. 3,992,158, U.S. Pat. No. 4,042,335, U.S. Pat. No. 4,144,306, U.S. Pat. No. 4,132,528, U.S. Pat. No. 4,050,898, U.S. Pat. No. 4,258,011, U.S. Pat. No. 4,275,152, U.S. Pat. No. 4,292,272 and so on.

The measuring reagent solution spotted onto the dry analytical element contains a reagent composition capable of producing an optically detectable substance such as dye in the presence of analyte. The reagent composition applicable to the invention includes compositions producing a dye by the oxidation of leuco dye (arylimidazole leuco dyes disclosed in U.S. Pat. No. 4,089,747, EP 0 122 641A, etc.), diazonium salts, compositions containing a compound producing a dye by coupling with other compound when it is oxidized (4-aminoantipyrines, phenols, naphthols, etc.), compositions composed of a compound capable of producing a dye in the presence of a reduced type coenzyme and an electron carrier, and the like.

As the leuco dye, there are triarylimidazole leuco dyes disclosed in U.S. Pat. No. 4,089,747, EP 0 122 641A, known triarylmethane leuco dyes and the like.

A dye may be formed by a dye-forming composition containing a condensation product between an oxidizable compound and a coloring agent. Examples of the oxidizable compound are benzidines, their homologues, p-phenylenediamines, p-aminophenols, aminoantiphyrines such as 4-aminoantipyrine and the like.

In the case of the dry analytical elements measuring enzyme activity, a self color-developing type substrate (e.g. paranitrophenylphosphate ester, paranitrophenylmaltpentaose, α-glutamylparanitroanilide) capable of releasing a color substance such as p-nitropenol can be incorporated into the hydrophilic polymer-layer or the spreading layer.

The reagent composition may contain an enzyme, and those disclosed from page 18 to page 20 of Japanese Patent KOKAI No. 62-138756 (EP 0 226 465A) are applicable to the invention. The reagent composition may be those utilizing immunological reaction (EP 0 310 940A).

A part of the reagent composition may be incorporated into a substantially uniform layer using a hydrophilic polymer as the binder. Examples of the hydrophilic polymer are gelatin and its derivatives (e.g. phthalated gelatin), cellulose derivatives (e.g. hydroxypropyl cellulose, carboxymethyl cellulose), agarose, acrylamide polymers, methacrylamide polymers, copolymers of acrylamide or methacrylamide and various vinyl monomer, polyvinylpyrrolidone, copolymers of vinylphyrrolidone and various vinyl monomer, and the like.

A part of the reagent composition may be incorporated into a porous layer. As a means for incorporating the reagent composition producing color in the presence of analyte into at least one porous layer, a suitable solutionor suspension of the reagent composition is impregnated with or coated onto the porous layer such as porous spreading layer, and then the porous layer is adhered to another water-permeable layer such as reagent layer by the method disclosed in U.S. Pat. No. 4,292,272 or the like. Alternatively, the porous layer may be first adhered to another water-permeable layer (e.g. under coating layer, adhesive layer, water absorption layer) by the method disclosed in U.S. Pat. No. 4,292,272 of the like, and then, the reagent composition solution or suspension is coated onto the porous layer.

For the impregnation or coating onto the porous layer, a known method can be utilized. For example, coating can be conducted selected from dip coating, doctor knife coating, hopper coating, curtain coating and the like.

A part of reagents may previously incorporated into the analytical element. It is preferable to incorporate previously common reagents regardless of analytical items. The common reagents include pH buffer, stabilizer for coloring agent or enzyme, and the like.

The object component (analyte) of a liquid sample to be analyzed may be a low molecular weight substance, an ion or a high molecular weight substance, and may be a hydrophilic substance or a hydrophobic substance. The analyte may be an enzyme, an antigen or an antibody. The antigen or antibody may be labeled with an enzyme or a fluorescent material, or bound to a polymer. The antigen may be hapten.

Examples of Analyte

Low Molecular Weight Substances: urea, uric acid, ammonia, creatinine, lactic acid, pyruvic acid, glucose, galactose, neutral fats, cholesterol, homoglobin, bilirubin.

Ions: calcium ion, potassium ion, sodium ion, chlorine ion.

High Molecular Weight Substances: protein (albumin, globulin, etc.), nucleic acid, lipoprotein.

Enzymes: amylase, phosphatase, lipase, lactate dehydrogenase, creatinine phosphokinase, alanine aminotransferase, asparagine aminotransferase.

The keypoint for achieving the high speed measurement in the invention is in that, by once substantially drying (not more than 1 mg/cm$^2$ preferably not more than 500 μg/cm$^2$) all spotted samples under a predetermined temperature, the dry analytical element can be preserved without denaturing and degrading the spotted samples until an optimum timing for spotting the measuring reagent solution and then measuring. By incorporating the drying process of spotted samples into handling processes, it is rendered possible that many analytical items can be measured at once at a high speed (optionally simultaneously by arranging a plurality of optical heads in parallel). Thereby, the measuring conditions can be optimized (for example, only specific items are measured collectively preferentially), and accordingly, to measure by a simple mechanism using compact measuring devices is possible to decrease troubles and the facilitate maintenance. Contrarily, in the solution method, it is necessary to conduct measurement immediately after mixing reagent with sample. As a result, when many items are measured in parallel, the apparatus becomes very complex and oversized.

EXAMPLE

An example of the analyzer of the invention is shown in FIG. 1. The analyzer is composed of one sample station 1 and two measuring stations 2, 3. Each movable sample tray 4 is formed of a glass plate 15 cm × 15 cm in size provided with rollers on the side ends of the underside, and travels on rails (not illustrated) provided on the upper side of the analyzer to stop at the position of each station. The sample-pipetting apparatus 5 for spotting samples and the reagent-pipetting apparatus 6 for spotting measuring reagent solutions are commercial pipetting appratuses in the XY type. Cups 9 for receiving samples or measuring reagent solutions are arranged circular on turntables 7, 8, and microtips 11 for taking a constant amount of a sample or a measuring reagent solution from a cup 9 to spot onto a dry analytical element 10 are arranged circular on the inside. An incubator is embedded in the upper part of the sample station 1. Measuring heads of 10 reflection optical densitometers are arranged in a row in the lateral direction above each measuring station 2, 3, and each row of the measuring heads is movable in the longitudinal direction.

As the analyzing method using the analyzer is as follows: First, a dry analytical element sheet 15 cm × 15 cm in size which does not contain reagents at all is set on the upper face of each movable sample tray. The dry analytical element is composed of a transparent support 14, and a hydrophilic polymer layer 15 and a porous spreading layer 16 which do not contain reagents laminated thereonto in this order. The movable sample tray is positioned at the sample station, and 10 samples are spotted onto the dry analytical element sheet by the pipetting apparatus at 10 positions per one sample in total 100 positions. The time necessary for spotting is 1 second for one spotting and 5 seconds for changing the microtip which is conducted at each change of samples to be spotted, and the total time necessary for spotting samples onto one sheet is 150 seconds. Subsequently, incubation is conducted at 37° C. for 3 minutes to dry the spotted samples. Then, the movable sample tray is moved to the measuring station 2 for 10 seconds, and measuring reagent solutions are spotted by the pipetting apparatus. The spotting is conducted by dividing into each analytical item, and the time necessary for spotting is 1 second for one spotting and 5 seconds for changing the microtip which is conducted at each change of measuring reagent solutions. Since total analytical items are 20 items, the total time necessary for spotting measuring reagent solutions onto one sheet is 200 seconds. A evaporation-preventing cover sheet 11 is place to each part spotted with a measuring reagent solution immediately. Instead of the evaporation-preventing cover sheet, another evaporation preventing member consisting of a ring magnet 12 and a metal ball 13 which closes the opening of the magnet 12. After spotting of measuring reagent solutions is finished at each row, the reflection optical densities of each row are measured at each 1 minute 1 after spotting up to 6 minutes. Meanwhile, the measuring heads travel each row successively. After the measurement is finished the analytical element is peeled and then removed. The time necessary for the removal is 10 seconds, and the total time necessary for analyzing 100 analyses was 910 seconds.

On the other hand, next movable sample tray reaches the sample station which becomes empty by the movement of the dry analytical element wherein the spotting and drying of samples have been finished, and spotting of samples and drying are conducted similarly. Then, the movable sample tray is moved to the measuring station 3. The measuring station 3 has the same structure as the measuring station 2, and spotting of measuring reagent solution and measurement are conducted similarly. By providing two measuring stations, the time staying at the sample station becomes rate-determining step, and 100 analyses can be conducted for 336 seconds.

Figure 2:
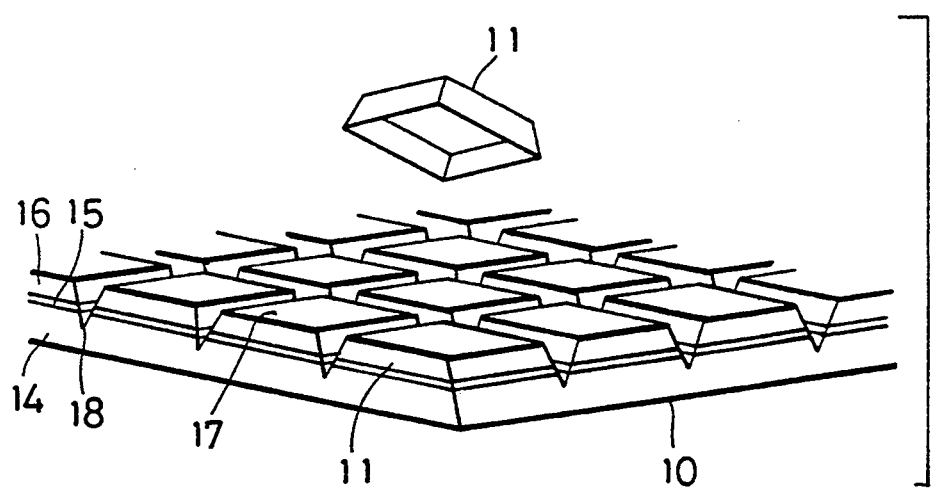
FIG. 2 is a partial perspective view of a dry analytical element which is applied to the invention. The dry analytical element is divided into respective reaction zones by grooves formed by heat cutting, and each reaction zone is fitted with a plastic cap as the evaporation-preventing member.

As shown in FIG. 2, the dry analytical element 10 can be divided into respective reaction zones 17 by grooves 18 formed by heat cut. In this example, each reaction zone 17 is covered by fitting a plastic cap of which peripheral end reaches the support as the evaporation-preventing member.

I claim:

1. A method for measuring a plurality of analytical samples using a high speed analyzer which comprises spotting of samples onto a dry analytical element comprising a plurality of reaction zones., one sample being spotted on each reaction zone and composed of a porous spreading layer, a hydrophilic polymer layer and a water-impermeable support laminated in this order, said dry analytical elements being positioned on a movable sample tray, introducing the thus spotted analytical elements to an incubator wherein the spotted samples are dried, spotting a plurality of measuring reagent solutions onto the dried analytical element and then subjecting the analytical element having the measuring reagent solution spotted thereon to measurement conditions to analyze the samples spotted thereon, attaching evaporation preventing members to the element having the reagent solution thereon to prevent evaporation of moisture from the thus spotted portions, and each reaction zone of the analytical element being formed, such that the spotted reagent solutions do not permeate into adjacent reaction zones and the reactions proceed independently at each reaction zones.

2. The method of claim 1 wherein the evaporation-preventing members are caps to cover the reaction zones up to the support.

3. The method of claim 1 wherein the evaporation-preventing members are film sealings.

4. The method of claim 1 wherein the area of each reaction zone is 20 to 200 mm$^2$.

5. The method of claim 1 wherein the measuring reagent solution contains a reagent composition capable of producing an optically detectable substance in the presence of analyte.

6. The method of claim 1 wherein the dry analytical element onto which the samples have been spotted is dried up to not more than 1 mg/cm$^2$ of moisture content.

7. The method of claim 1 wherein the porous spreading layer is formed of a thermoplastic material and the dry analytical element is divided by grooves formed by heat cutting to reach the support.

8. The method of claim 7 wherein the grooves are formed by fusion.

* * * * *